(12) United States Patent
Carlton et al.

(10) Patent No.: US 9,220,889 B2
(45) Date of Patent: Dec. 29, 2015

(54) DIRECTIONAL ELECTRODE DEVICES WITH LOCATING FEATURES

(75) Inventors: Keith Carlton, Cleveland, OH (US); Alan Greszler, Bay Village, OH (US); Scott Kokones, Cleveland, OH (US)

(73) Assignee: Intelect Medical, Inc., Cleveland, OH (US)

( * ) Notice: Subject to any disclaimer, the term of this patent is extended or adjusted under 35 U.S.C. 154(b) by 1081 days.

(21) Appl. No.: 12/029,141

(22) Filed: Feb. 11, 2008

(65) Prior Publication Data

US 2009/0204192 A1    Aug. 13, 2009

(51) Int. Cl.
*A61N 1/05* (2006.01)
*A61N 1/36* (2006.01)

(52) U.S. Cl.
CPC ............ *A61N 1/0529* (2013.01); *A61N 1/0534* (2013.01); *A61N 1/0539* (2013.01); *A61N 1/36182* (2013.01); *A61N 1/0551* (2013.01)

(58) Field of Classification Search
CPC ...... A61N 1/05; A61N 1/0551; A61N 1/0529
USPC ....................................................... 607/116
See application file for complete search history.

(56) References Cited

U.S. PATENT DOCUMENTS

| 5,127,403 | A | 7/1992 | Brownlee |
|---|---|---|---|
| 5,360,441 | A | 11/1994 | Otten |
| 5,480,421 | A | 1/1996 | Otten |
| 5,522,875 | A | 6/1996 | Gates et al. |
| 5,769,858 | A | 6/1998 | Pearson et al. |
| 5,824,030 | A | 10/1998 | Yang et al. |
| 7,050,855 | B2 | 5/2006 | Zeijlemaker et al. |
| 7,174,219 | B2 | 2/2007 | Wahlstrand et al. |
| 7,181,288 | B1 | 2/2007 | Rezai et al. |
| 2002/0183817 | A1 | 12/2002 | Van Venrooij et al. |
| 2004/0098074 | A1 | 5/2004 | Erickson et al. |
| 2005/0171587 | A1* | 8/2005 | Daglow et al. ................ 607/116 |

FOREIGN PATENT DOCUMENTS

| EP | 0832667 | 4/1998 |
|---|---|---|
| EP | 1602393 | 12/2005 |
| WO | 20050053789 | 6/2005 |

OTHER PUBLICATIONS

PCT International Search Report and Written Opinion dated Jul. 1, 2009.

* cited by examiner

*Primary Examiner* — Christopher D Koharski
*Assistant Examiner* — Michael D Abreu
(74) *Attorney, Agent, or Firm* — Lowe Graham Jones PLLC; Bruce E. Black

(57) ABSTRACT

Electrode devices having directional electrodes for use in deep brain stimulation or other uses. In one aspect, an electrode assembly comprises an elongate lead and a lead guide that are engageable with each other in a coaxial relationship. When the elongate lead and the lead guide are engaged with each other, the two components are rotationally fixed in relation to each other. In another aspect, an elongate lead comprises a radiologically-visible feature for indicating the orientation of the elongate lead. In yet another aspect, an electrode system is capable of determining the position and/or orientation of an electrode positioned within a body. In other aspects, methods for electrically stimulating a target site in the body are disclosed.

13 Claims, 11 Drawing Sheets

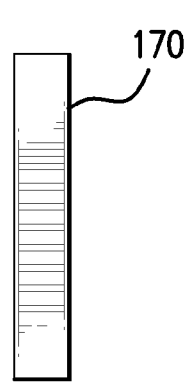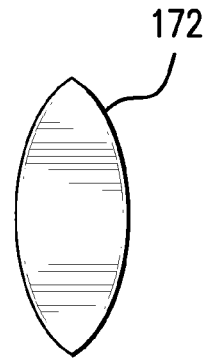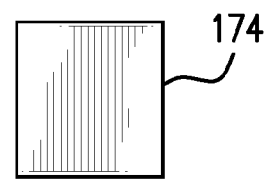
FIG.6A    FIG.6B    FIG.6C
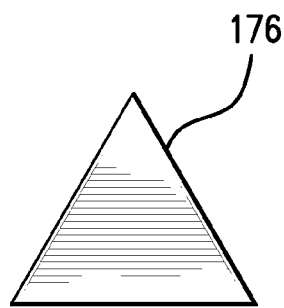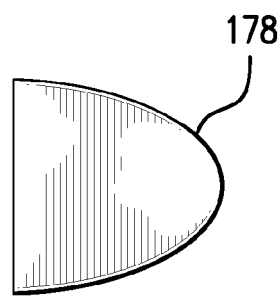
FIG.6D    FIG.6E

DIRECTIONAL ELECTRODE DEVICES WITH LOCATING FEATURES

TECHNICAL FIELD

The present invention relates to medical devices, and in particular, electrode devices for electrical stimulation.

BACKGROUND

Implantable pulse generators for stimulating tissue are being used in increasing numbers to treat a wide variety of medical conditions. In many cases, electrical stimulation pulses are conveyed from a pulse generator to a desired stimulation site by an implanted lead with exposed electrodes. In order to achieve the desired effects from the delivery of stimulating pulses, it is important that the lead is properly positioned so that optimal stimulating energy is applied to a desired site. While this is true for many different kinds of stimulation therapies, lead positioning is especially critical in the area of neurological stimulation.

Stylets are used in the field of electrical stimulation for guiding and properly placing leads. Leads that utilize stylets for guidance are subject to the problem of lead twisting or torquing during placement. Lead twisting or torquing often results in the lead rotating with respect to the stylet and possibly becoming misaligned. Precise knowledge of the location and position of the lead and electrodes providing the stimulation, along with its volume of activation relative to the target site and surrounding structures is critical to treatments, particularly when providing neurological stimulation to an area of a patient's brain.

While conventional DBS systems have advanced rehabilitation and treatment in a number of areas, certain challenges remain and there is a need for electrode devices to meet these challenges.

SUMMARY

In a first aspect, the present invention provides an electrode assembly comprising: (a) an elongate lead having at least one directional electrode positioned at a distal portion thereof and (b) a lead guide that is slidably engageable with the elongate lead in a coaxial relationship. The elongate lead and the lead guide are rotationally fixed when they are engaged with each other.

In a second aspect, the present invention provides an elongate lead comprising: (a) at least one directional stimulation electrode positioned on a distal portion of the elongate lead; and (b) at least one radiologically-visible feature for indicating the orientation of the at least one directional stimulation electrode when viewed under radiologic imaging.

In a third aspect, the present invention provides an electrode system comprising: (a) an elongate lead having at least one directional electrode positioned at a distal portion of the elongate lead; and (b) a position determining apparatus for determining the position and/or orientation of the at least one directional electrode when the electrode is positioned in a body.

In other aspects, the present invention provides methods for electrically stimulating a target site in the body using various electrode devices.

BRIEF DESCRIPTION OF THE DRAWINGS

FIG. 1A shows a side view of an elongate lead. FIG. 1B shows a side view of a stylet. FIG. 1C shows a side view of the elongate lead with the stylet inserted therein. FIG. 1D shows a transverse cross-section view of the assembly taken at arrow 1 in FIG. 1C.

FIG. 2A shows a perspective view of the stylet. FIG. 2B shows a distal end view of the stylet.

FIG. 3A shows a partial cross-section side view of the electrode assembly with an elongate lead inserted within a cannula. FIG. 3B shows a transverse cross-section view of the assembly taken at arrow 2 in FIG. 3A.

FIGS. 6A-6E show transverse cross-sections views of a stylet according to various alternate embodiments of the electrode assembly.

FIG. 7A shows a partial cross-section side view of the assembly. FIG. 7B shows a transverse cross-section view of the assembly taken at arrow 3 in FIG. 7A, with the gripping elements in a released position. FIG. 7C shows a transverse cross-section view of the assembly taken at arrow 3 in FIG. 7A, with the gripping elements in a gripping position.

FIG. 9A shows the elongate lead with the radiopaque feature facing out of the page. FIG. 9B shows the elongate lead rotated 180° from the view shown in FIG. 9A such that the radiopaque feature faces into the page.

FIG. 10A shows the elongate lead with the radiopaque feature facing out of the page. FIG. 10B shows the elongate lead rotated 180° from the view shown in FIG. 10A such that the radiopaque feature faces into the page.

FIG. 11A shows the elongate lead with the radiopaque feature facing out of the page. FIG. 11B shows the elongate lead rotated 180° from the view shown in FIG. 11A such that the radiopaque feature faces into the page.

FIG. 12A shows the elongate lead with the radiopaque feature facing out of the page. FIG. 12B shows the elongate lead rotated 180° from the view shown in FIG. 12A such that the radiopaque feature faces into the page.

FIG. 13A shows the elongate lead in a straight configuration. FIG. 13B shows the elongate lead in a twisted configuration.

FIG. 14A shows the elongate lead in one rotational orientation; and FIG. 14B shows the elongate lead rotated 180° from the view shown in FIG. 14A.

DETAILED DESCRIPTION

Figure 1A:
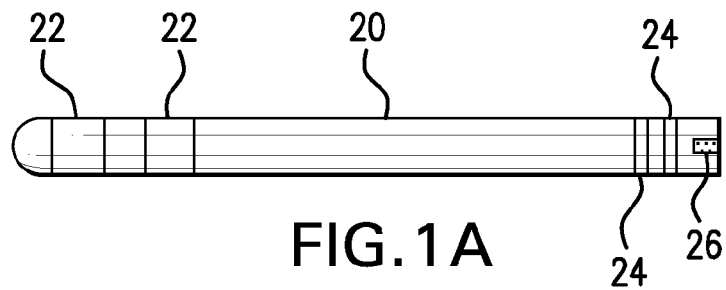
FIGS. 1A-1D show various views of an electrode assembly according to an embodiment of the present invention.

In an embodiment, the present invention provides methods, systems and devices for the accurate placement of leads in the brain and/or other parts of the nervous system. In a first aspect, the present invention provides an electrode assembly comprising a first component which is an elongate lead having at least one directional electrode positioned at a distal portion thereof. As used herein, a "directional electrode" refers to an electrode on an elongate lead in which the electrode extends less than 360° about the body of the elongate lead. The assembly further includes a second component that is a lead guide that is slidably engageable with the elongate lead in a coaxial relationship. Accordingly, the elongate lead may have an inner channel with the lead guide being insertable into the inner channel of the elongate lead; or alternatively, the lead guide may have an inner channel with the elongate lead being insertable into the inner channel of the lead guide. According to this embodiment, the elongate lead and the lead guide are rotationally fixed when they are engaged with one another. As used herein, the term "rotation," when used in relation to the elongate lead or the lead guide, refers to rotation about the central longitudinal axis of the component. By being rotationally fixed in relation to each other, rotation of the lead guide will cause rotation of the elongate lead, and vice versa. Similarly, if the lead guide is not rotated, this will cause non-rotation of the elongate lead. Accordingly, the elongate lead and the lead guide, although separate components, rotate as a single unit. Since the lead guide is designed to transfer any rotational torque (e.g., provided manually or by other means by the user at the proximal end of the lead guide) to the elongate lead, the lead guide may have any of various features for facilitating this function, such as handles and alignment markers indicating the alignment of the two components.

The rotational fixation between the elongate lead and the lead body may be achieved by any of various mechanisms to restrain rotational movement of the elongate lead in relation to the lead guide. Such mechanisms permit a rotational force placed on the proximal end of the lead guide to be transferred along the length of the lead thereby causing the proximal and distal ends of the lead to rotate together in unison. Non-limiting examples of locking mechanisms to achieve this restraint in rotational movement, include male/female connections, threadable engagement, or interference fit. In certain embodiments, the elongate lead comprises a first rotation locking structure, and the lead guide comprises a second rotation locking structure. The first rotation locking structure and the second rotation locking structure releasably engage and cooperate with each other to restrain rotational movement of the elongate lead in relation to the lead guide. The rotation locking structures may be located on any of various portions of the elongate lead or lead guide, including inner surfaces, outer surfaces, distal portions, or proximal portions so long as torque is transferred to the elongate lead when the lead guide is rotated. Therefore, lead guide and the elongate lead can be configured to be mated such that rotation of the proximal end of the lead guide causes the proximal and distal ends of the elongate lead to also rotate.

In some embodiments, the first rotation locking structure and the second rotation locking structure have complementary geometries (i.e. a male/female relationship), allowing a mating interaction between the two locking structures. For example, one component (i.e., the lead guide or the elongate lead) can have a protruding structure and the other component can have a recessed structure, wherein the protruding structure interlocks with the recessed structure in such a way as to limit rotational movement of the elongate lead relative to the lead guide. The protruding structures may be, for example, ridges, bumps, ribs, and the like. The recessed structure may be, for example, grooves, channels, pits, cavities, and the like. The female structure can either be part of the elongate guide or the lead body. Similarly, the male structure can be part of the elongate guide or the lead body. Furthermore, the locking structures can either be made of a separate material than the component to which they are a part of or they can be made of the same material. As such, the locking structures and their respective component can form a single unitary structure or the two can be separate elements that are coupled together.

Figure 1B:
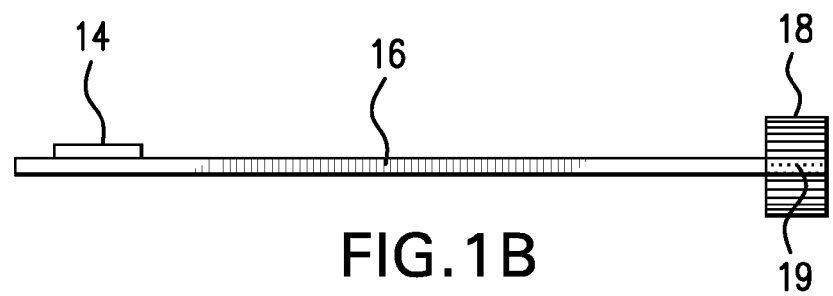
Figure 1C:
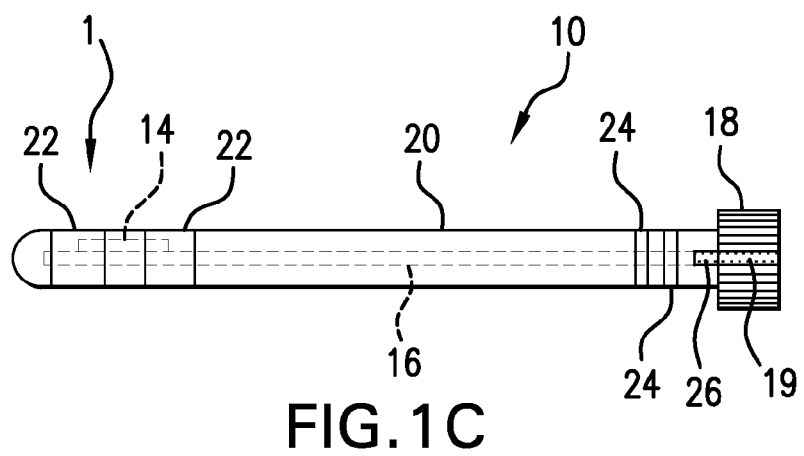
Figure 1D:
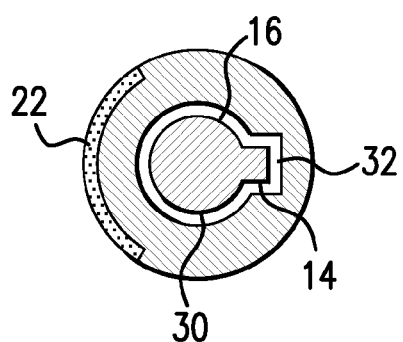

For example, referring to the embodiment shown in FIGS. 1A-1D, an electrode assembly 10 comprises an elongate lead 20 and a lead guide in the form of stylet 16. In this embodiment, elongate lead 20 has directional stimulation electrodes 22 positioned at a distal portion of elongate lead 20. As seen in FIG. 1D, directional electrodes 22 extend 120° about the body of elongate lead 20, however, the directional electrode can extend any degree about the body of lead 20 that is less than 360°. Elongate lead 20 also has electrical contacts 24 for coupling with an external stimulator or implantable pulse generator. Each of contacts 24 independently supply electrical connectivity to electrodes 22. Elongate lead 20 has an inner channel 30 which is configured to receive stylet 16. Stylet 16 is made of a relatively stiff material and is configured to be inserted within inner channel 30 of elongate lead 20. In this embodiment, the first rotation locking structure is a key 14 and is rigidly fixed onto or otherwise integral with a distal portion of stylet 16. Inner channel 30 of elongate lead 20 has the second locking structure, which is a recess 32 contoured to receive key 14 in a locking secure manner and which extends along the length of elongate lead 20. The recess can be made of the same material as the elongate lead, such as polyurethane, or can be a separate structure applied to the elongate lead, such as a metal insert. A handle 18 can be fixed to the proximal end of stylet 16 to allow the user to apply torque to stylet 16, which is transferred throughout the length of lead 20 thereby causing the proximal and distal ends of the lead to rotate in unison. Of course, stylet 16 could also be rotated by means other than manual means, such as electrically or telemetrically.

In operation, the distal end of elongate lead 20 is inserted into the target site. Stylet 16 is inserted into inner channel 30 of elongate lead 20. To ensure alignment of key 14 and recess 32, elongate lead 20 and stylet 16 can both have orientation indicators, which in the embodiment shown in FIGS. 1A-1C are marks parallel to the longitudinal axis of elongate lead 20 and stylet 16. Specifically, referring to FIGS. 1A-1C, the proximal end of elongate lead 20 can have an orientation indicator 26 and handle 18 of stylet 16 can have an orientation indicator 19, with orientation indicator 26 aligned with recess 32 and orientation indicator 19 aligned with key 14. When orientation indicator 26 is aligned with orientation indicator 19, a straight line is formed, which indicates that key 14 is aligned with recess 32. Of course, other configurations of orientation indicators 26 and 19 are also possible. Because of the mating of key 14 and recess 32, elongate lead 20 is rotationally locked with stylet 16. Thus, as elongate lead 20 is being positioned at the target site, the user can turn handle 18 of stylet 16 to cause elongate lead 20 to rotate accordingly, allowing the user to adjust the directional orientation of directional electrodes 22. One or more of directional electrodes 22 can then be activated to provide electrical stimulation to the target site.

Figure 2A:
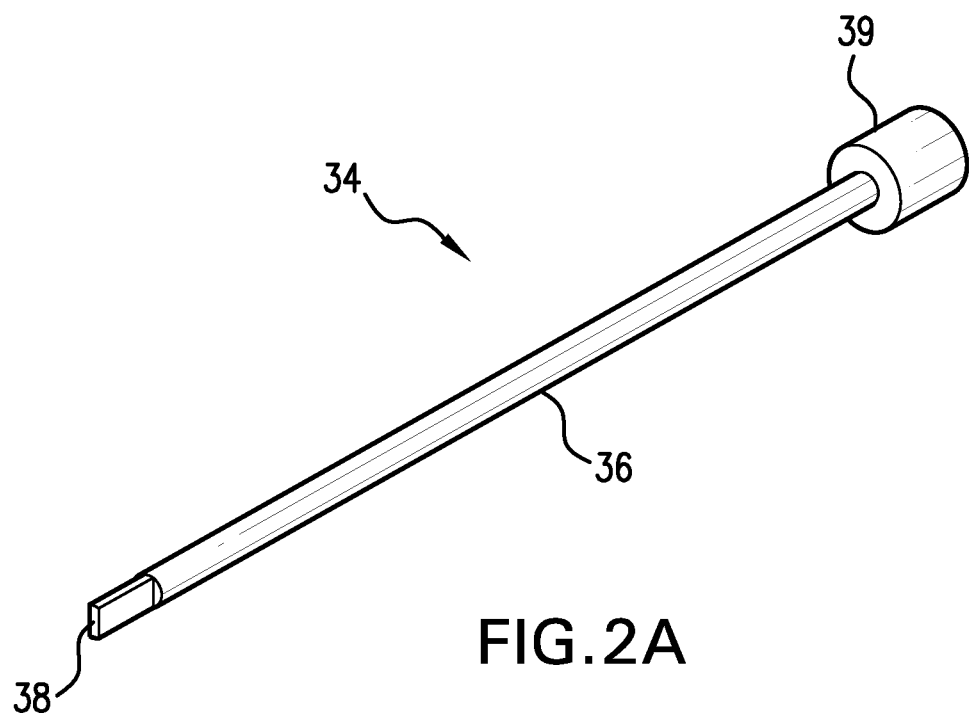
FIGS. 2A and 2B show a stylet according to another embodiment.
Figure 2B:
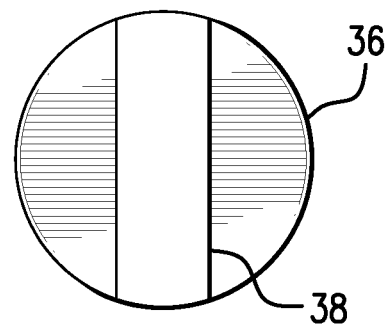

Other configurations for the stylet and/or key are also possible. For example, referring to the embodiment shown in FIGS. 2A and 2B, a stylet 34 has a shaft 36 and a key 38 located at the distal tip of shaft 36. As seen in the end-view of stylet 34 in FIG. 2B, in this embodiment, the maximum width of key 38 is no greater than the diameter of shaft 36. An elongate lead for use with stylet 34 can have a distally-located recess that is complementary to key 38.

Figure 3A:
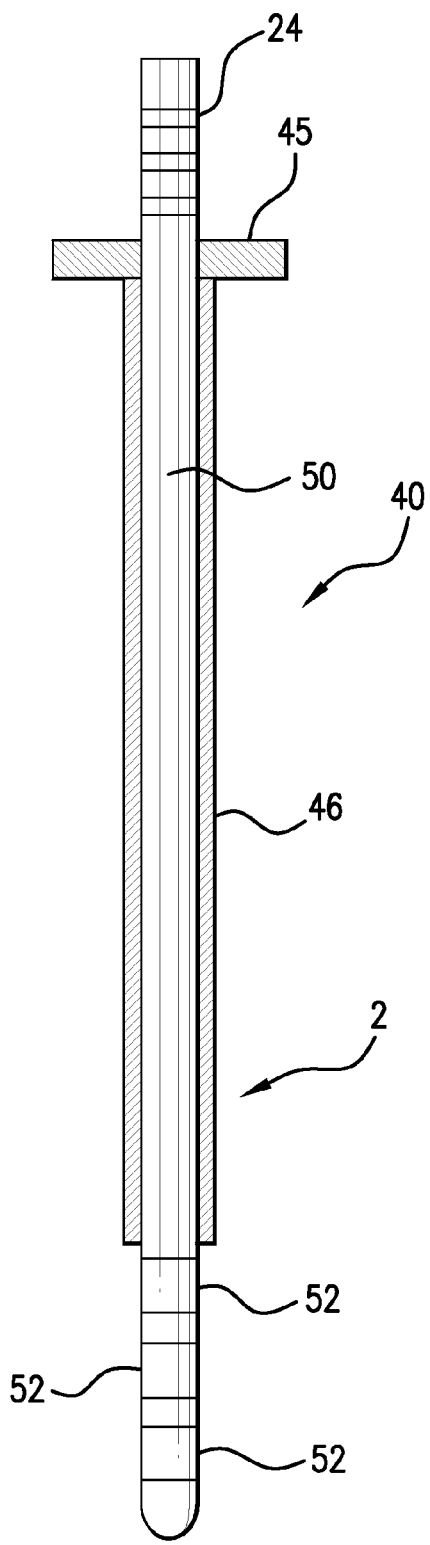
FIGS. 3A and 3B show an electrode assembly according to another embodiment.
Figure 3B:
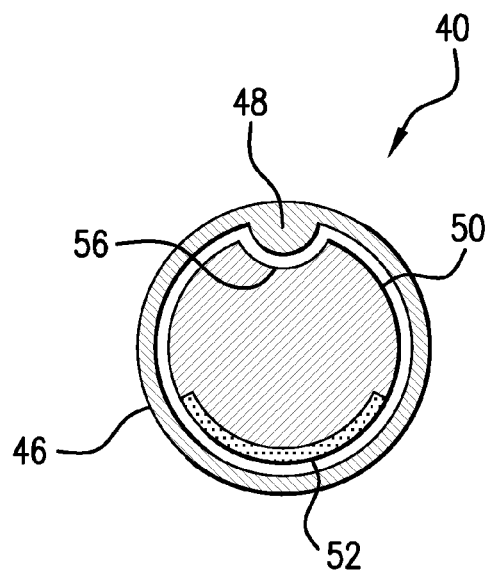

In another example of the electrode assembly, referring to the embodiment shown in FIGS. 3A and 3B, an electrode assembly 40 comprises an elongate lead 50 and a lead guide in the form of cannula 46. In this embodiment, the lead guide is disposed about the outer surface of the elongate lead, whereas in the embodiment illustrated in FIG. 1A-1D, the elongate lead is disposed about the outer surface of the lead guide. As with the embodiment described above, elongate lead 50 has directional stimulation electrodes 52 positioned at a distal portion of elongate lead 50. As seen in FIG. 3B, directional electrodes 52 extend 120° around the body of elongate lead 50, but can extend to other degrees less than 360° about the body of the lead. Elongate lead 50 also has electrical contacts 24 for coupling to an external stimulator or implantable pulse generator. Each of contacts 24 independently supply electrical connectivity to electrodes 52. On its outer surface, elongate lead 50 has a first rotation locking structure that is a groove 56 which is contoured to receive a second rotation locking structure that is a ridge 48 on the inside surface of cannula 46.

In this embodiment, cannula 46 has an inner channel configured to receive elongate lead 50. As stated above, on its inside surface, cannula 46 comprises a ridge 48 which extends along the length of cannula 46. Ridge 48 is contoured to mate with groove 56 of elongate lead 50 to form a locked relationship. A handle 45 can be fixed to the proximal end of cannula 46 to allow the user to manually rotate cannula 46. Of course, cannula 46 could also be rotated by other means, such as electrically or telemetrically.

In operation, the distal end of cannula 46 is inserted into the patient's body. Elongate lead 50 is inserted into the inner channel of cannula 46 such that groove 56 is aligned with ridge 48. Because of the mating of ridge 48 and groove 56, elongate lead 50 is rotationally locked with cannula 46. Thus, as elongate lead 50 is being positioned at the target site, the user can turn handle 45 of cannula 46 to cause elongate lead 50 to rotate accordingly, allowing the user to adjust the directional orientation of directional electrodes 52. One or more of directional electrodes 52 can then be activated to provide electrical stimulation to the target site.

Figure 4:
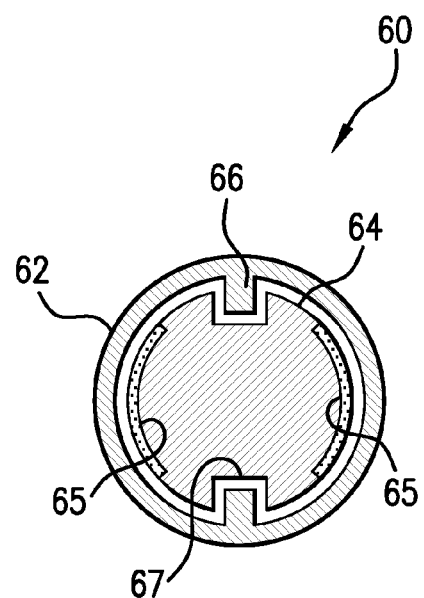
FIG. 4 shows a transverse cross-section view of an electrode assembly according to yet another embodiment.

In another example, referring to the embodiment shown in FIG. 4, an electrode assembly 60 comprises an elongate lead 64 and a lead guide in the form of a cannula 62. Cannula 62 has an inner channel configured to receive elongate lead 64. A pair of first rotational locking structures that are keys 66 are oppositely positioned on the inside surface of cannula 62. Keys 66 are contoured to mate with second locking structures, which are a pair of oppositely positioned grooves 67 on elongate lead 64. Grooves 67 are contoured to mate with keys 66 to form a locked relationship. Elongate lead 64 can have a pair of 120° directional stimulation electrodes 65 positioned on opposite sides of elongate lead 64. Of course, other directional electrodes can also be used. In operation, electrode assembly 60 is used in a manner similar to that described for the above-mentioned embodiments.

Figure 5:
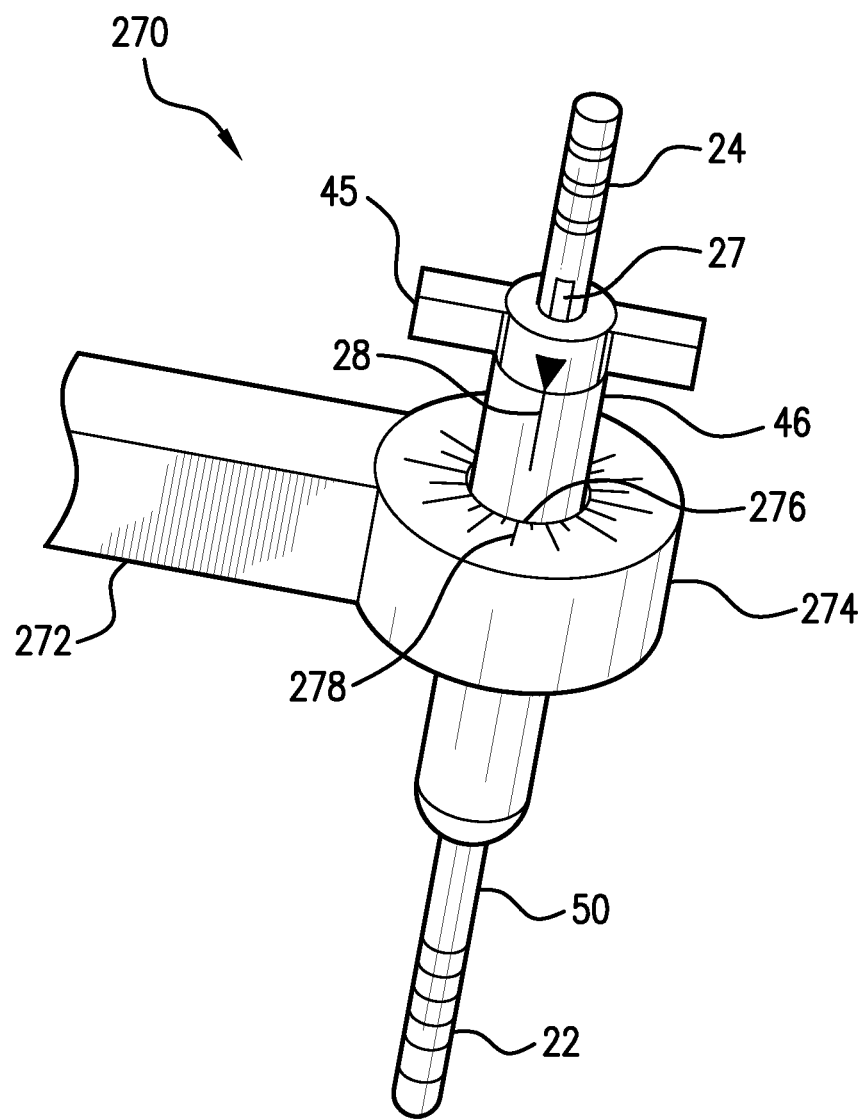
FIG. 5 shows a perspective view of a cannula holder according to an embodiment.

In some embodiments, the electrode assembly further comprises a lead guide holder for holding the lead guide. The lead guide holder has a rotational indicator that indicates the rotational orientation of the elongate lead and/or lead guide in relation to a fixed point of reference (e.g., a stereotactic headframe). For example, referring to the embodiment shown in FIG. 5, the electrode assembly of FIGS. 3A and 3B above may further include a cannula holder 270 which is moveably attached to a stereotactic headframe (not shown). As such, cannula holder 270 can move in various axes, directions, or rotational planes on the stereotactic headframe. Cannula holder 270 has an arm 272, which is attached to the stereotactic headframe, and a ring 274 with a bore 276 through which cannula 46 is inserted. On ring 274 are a series of evenly-spaced tics 278 positioned around the circumference of bore 276. Tics 278 indicate the rotational orientation of cannula 46 with respect to an orientation indicator 28 that is aligned with orientation indicator 27 on electrode lead 50. This orientation information may be entered into a coordinate mapping system (such as that described below) and used in combination with the fiducial parameters provided by the stereotactic headframe for mapping of the position and orientation of the elongate lead and/or electrode in relation to structures in the brain. Other rotational indicators could also be used for indicating the rotational orientation of the elongate lead and/or lead guide in relation to a fixed point of reference (e.g., a stereotactic headframe).

Of course other configurations of the first and second rotation locking structures are contemplated. In other words, any embodiments are contemplated where one of the components has a portion that can be securely attached to another portion of the other component to prevent rotational movement of one component relative to the other. For example, the stylet can have an irregularly shaped tip as the second rotation locking structure that locks into a receptacle, which serves as the first rotation locking structure, at the distal end of the elongate lead. The first and/or second rotation locking structures need not extend the entire length of the elongate lead.

FIGS. 6A-E show different non-circular cross-sectional shapes for at least a portion of a stylet and a corresponding receptacle of an elongate lead according to embodiments of the present invention. The cross-sections in FIGS. 6A-E are taken along a plane perpendicular to the longitudinal axis of the stylet. A rectangle 170, an ellipse 172, a square 174, a triangle 176 and a general triangular shape with a rounded surface 178 are shown in FIGS. 6A-E, respectively. Other non-circular cross sections may also be provided. These non-circular cross-sections, along with their corresponding receptacles, may extend the length of the stylet and/or elongate lead or may be provided at the proximal ends and/or the distal ends of the stylet and the elongate lead or may be provided at other locations such that a sufficiently uniform force is transferred along the length of the stylet to the elongate lead thereby causing the proximal ends and distal ends of the stylet and the elongate lead to rotate together. Accordingly, the ends of the stylet and the elongate lead do not become misaligned.

In certain embodiments, the lead guide comprises one or more gripping elements to provide the rotational fixation between the elongate lead and the lead guide. The gripping element(s) is designed to frictionally engage the elongate lead. In some embodiments, the lead guide further comprises an activation mechanism for causing the gripping elements to engage the elongate lead, to release the elongate lead, and/or to lock the gripping elements in their engaged or released positions. Any of various activation mechanisms may be used for this particular function, including mechanical (e.g., using a slide, pull, or button actuation), pneumatic, or hydraulic mechanisms.

Figure 7A:
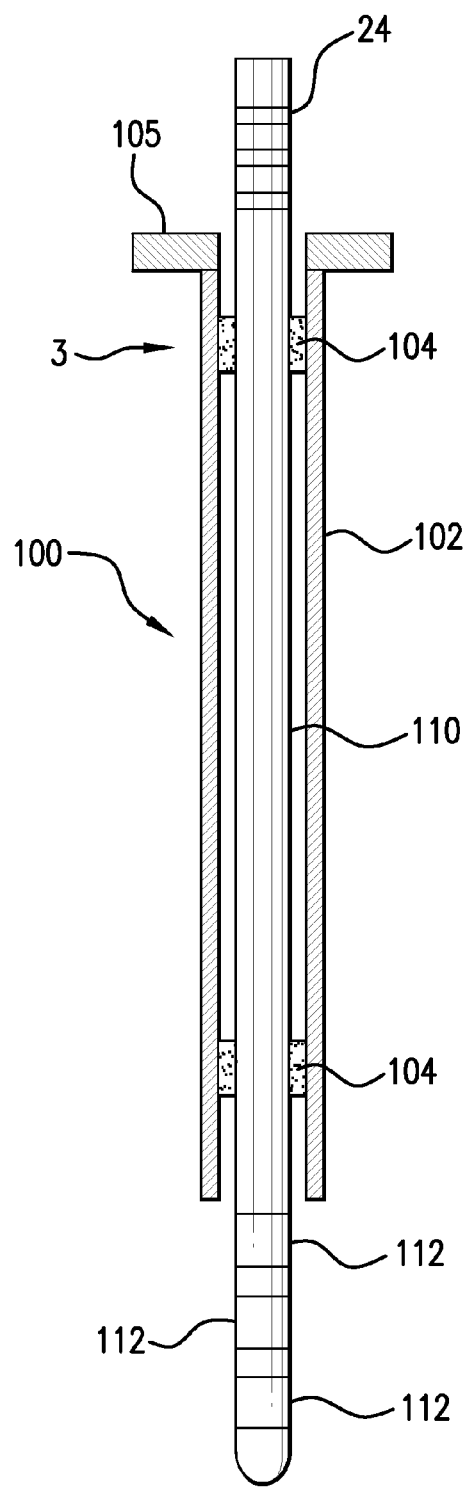
FIGS. 7A-7C show an electrode assembly according to yet another embodiment.
Figure 7B:
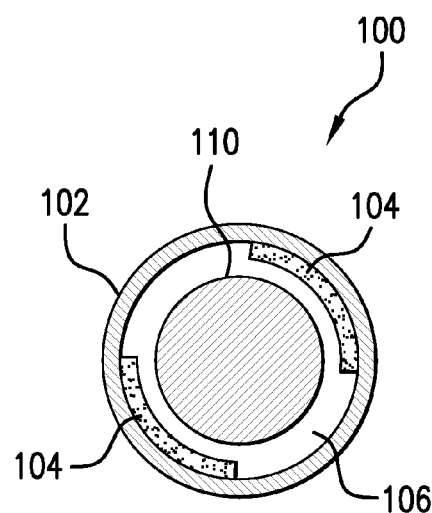
Figure 7C:
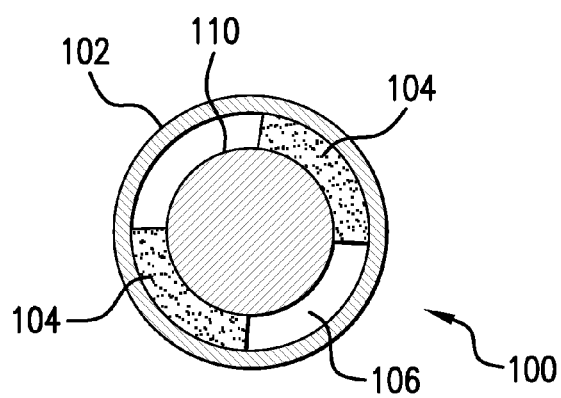

For example, referring to the embodiment shown in FIGS. 7A-7C, an electrode assembly 100 comprises an elongate lead 110 and a lead guide as cannula 102. Elongate lead 110 has directional stimulation electrodes 112 positioned at a distal portion of elongate lead 110 and contacts 24 at a proximal portion of elongate lead 110. Cannula 102 has an inner channel 106 configured to receive elongate lead 110. At proximal and distal portions, cannula 102 has gripping elements 104 which are designed to frictionally engage elongate lead 110, thereby restraining rotational movement of elongate lead 110 relative to cannula 102. Referring to FIGS. 7B and 7C, the pair of proximally located gripping elements 104 are positioned on opposite sides of the inner surface of cannula 102. Likewise, the pair of distally located gripping elements 104 are also positioned on opposite sides of the inner surface of cannula 102. By an actuation mechanism (not shown), gripping elements 104 may alternately engage elongate lead 110 (see FIG. 7C) or release elongate lead 110 (see FIG. 7B). A handle 105 can be fixed to the proximal end of cannula 102 to allow the user to manually rotate cannula 102. Of course, the cannula could be rotated by other means as well.

In operation, the distal end of cannula 102 is inserted into the patient's body. With gripping elements 104 in the released position, elongate lead 110 is inserted into inner channel 106 of cannula 102. After further advancement and positioning of elongate lead 110 in the patient's body, the user can actuate gripping elements 104 to engage and rotationally fix elongate lead 110. Then, when the user turns handle 105 on cannula 102, elongate lead 110 will rotate accordingly, allowing the user to adjust the directional orientation of directional electrodes 112. One or more of directional electrodes 112 can then be activated to provide electrical stimulation to the target site.

Figure 8:
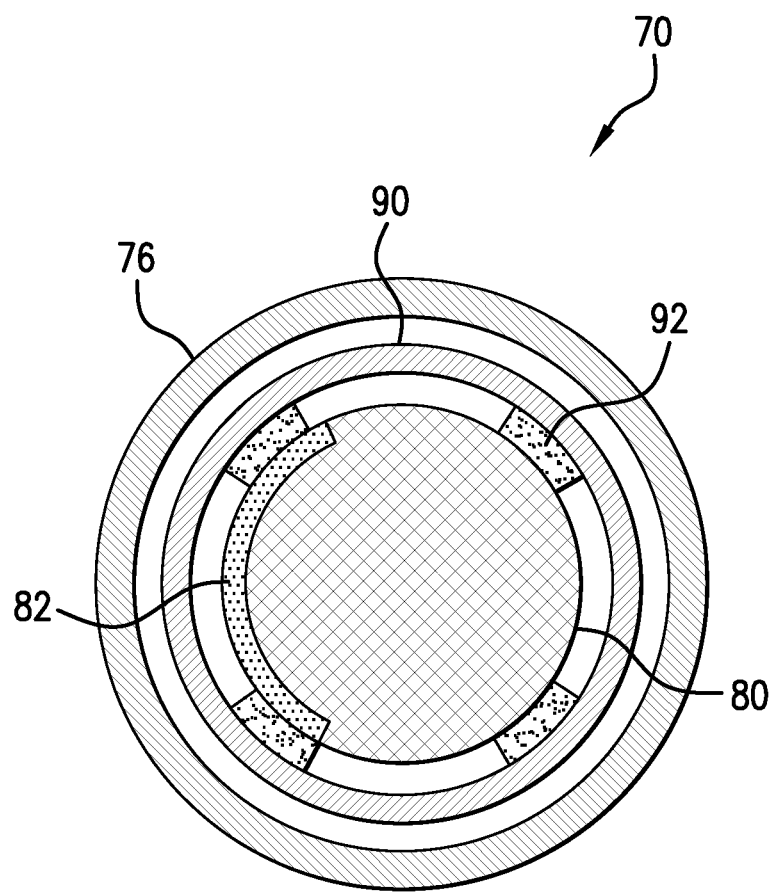
FIG. 8 shows a transverse cross-section view of an electrode assembly according to yet another embodiment.

In certain embodiments, the lead guide is a delivery structure that is designed to be positioned between the elongate lead and a cannula. The delivery system may engage the elongate lead using the mating mechanisms or gripping mechanisms described above. For example, referring to the embodiment shown in FIG. 8, an electrode assembly 70 comprises an elongate lead 80 and a lead guide as delivery structure 90. Cannula 76 has an inner channel configured to receive elongate lead 80 and delivery structure 90. Elongate lead 80 has a directional stimulation electrode 82 extending around the body of elongate lead 80. Delivery structure 90 is positioned between elongate lead 80 and cannula 76. As such, delivery structure 90 is configured to be insertable within the inner channel of cannula 76. Delivery structure 90 also has an inner channel which is configured to receive elongate lead 80. On its inner surface, delivery structure 90 has gripping elements 92 which frictionally engage elongate lead 80.

In operation, the distal end of cannula 76 is inserted into the patient's body. Then, delivery structure 90 (containing elongate lead 80, which is frictionally engaged with delivery structure 90 through gripping elements 92) is inserted into the inner channel of cannula 76. Because delivery structure 90 is rotationally locked with elongate lead 80, the user can turn delivery structure 90 to cause elongate lead 80 to rotate in concert accordingly, allowing the user to adjust the directional orientation of directional electrode 82. Directional electrode 82 can then be activated to provide electrical stimulation to the target site.

In an alternate embodiment, delivery structure 90 may have additional gripping elements which frictionally engage cannula 76. In this case, cannula 76 is rotationally locked with delivery structure 90, which in turn, is rotationally locked with elongate lead 80. As such, the user can turn cannula 76 to cause elongate lead 80 to rotate in concert, allowing the user to adjust the directional orientation of directional electrode 82.

The gripping element(s) may have any of various shapes, sizes, configurations, textures, and material compositions suitable for performing the above-described function. For example, the gripping element(s) may be formed of a deformable material, such as a soft thermoplastic material (e.g., silicone or polyurethane) and shaped to conform to the contours of the elongate lead. Alternatively, the gripping elements could comprise a more rigid base that is padded with a softer material such as silicone or polyurethane to prevent damage to the lead.

The gripping element(s) may be located at any of various positions on the lead guide, including the outer surface, proximal portions, or distal portions of the lead guide. The gripping element(s) and the lead guide may form a single unitary structure, or the two components may be separate units that are coupled together. Further, when more than one gripping element is employed, the gripping elements can be placed in different positions relative to each other so long as they collectively perform their intended function. For example, two or more gripping elements may be arranged in opposition to each other such that they engage opposite sides of the elongate lead, or the gripping element(s) may circumferentially surround the elongate lead.

This first aspect of the present invention may be combined with any of the features in the second and/or third aspects of the present invention.

In a second aspect, the present invention provides an elongate lead having one or more radiologically-visible features that indicate the rotational orientation of the directional electrode under radiologic imaging. The radiologically-visible feature may be radiolucent, radiopaque, or otherwise, so long as the feature is visible under radiologic imaging. The radiologic imaging may be any of various imaging modalities that are used to view an object inserted into a patient's body, including x-ray, x-ray fluoroscopy, CT scan, or MRI.

In certain embodiments, the radiologically-visible feature has a shape that is asymmetric with respect to the central longitudinal axis of the elongate lead. By having a shape that is asymmetric with respect to the central longitudinal axis of the elongate lead, the image of the feature under radiologic imaging will vary with the rotation of the elongate lead with respect to the particular view. For example, when viewed directly face-on, the feature will have one image; and when the elongate lead is rotated 180°, the see-through view of the feature will have a different (flipped) image. This allows the user to determine and/or adjust the rotational orientation of the directional electrode under radiologic imaging.

Figure 9A:
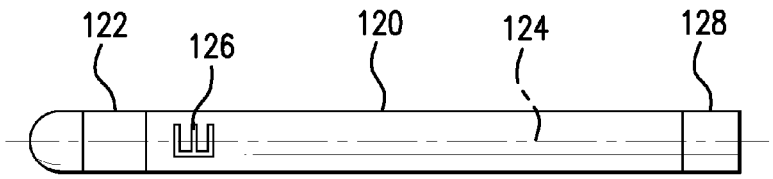
FIGS. 9A and 9B show side views of an elongate lead according to an embodiment of the present invention.
Figure 9B:
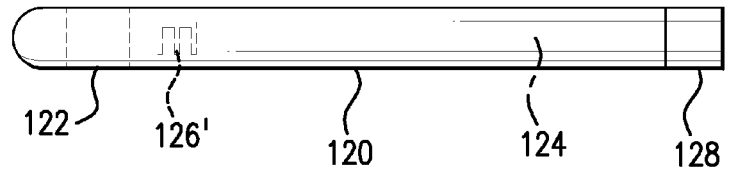

For example, referring to the embodiment shown in FIGS. 9A and 9B, an elongate lead 120, with a central longitudinal axis 124, has a radiopaque feature in the form of marking 126 which is asymmetric with respect to central longitudinal axis 124. Elongate lead 120 has a directional stimulation electrode 122 that extends 120° around the body of elongate lead 120 and an electrical contact 128 to supply electrical connectivity to electrode 122. In FIG. 9A, elongate lead 120 is rotated such that directional electrode 120 is facing out of the page (i.e., direct face-on view), and in FIG. 9B, elongate lead 120 is rotated 180° such that directional electrode 122 is facing into the page (i.e., see-through view). As such, the image of marking 126 seen in FIG. 9A is different from the flipped image 126' of marking 126 see in FIG. 9B. In operation, elongate lead 120 is positioned in the body and viewed under x-ray fluoroscopy. Since marking 126 is aligned with directional electrode 122, by visualizing marking 126 at various viewpoints under x-ray fluoroscopy, the user is able to determine the orientation of directional electrode 122 and make any necessary adjustments. Directional electrode 122 is then activated to provide electrical stimulation to the target site.

Figure 10A:
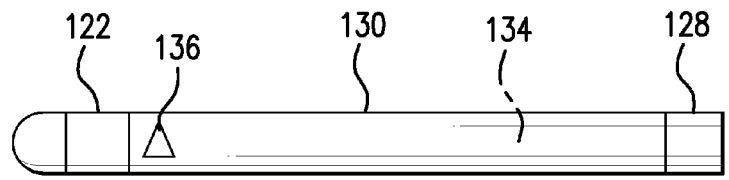
FIGS. 10A and 10B show side views of an elongate lead according to another embodiment.
Figure 10B:
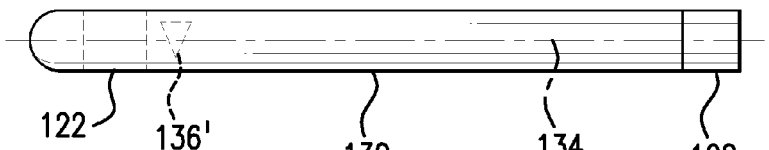
Figure 11A:
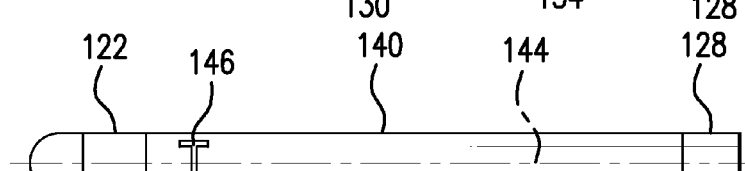
FIGS. 11A and 11B show side views of an elongate lead according to yet another embodiment.
Figure 11B:
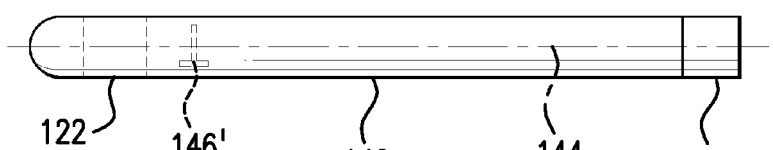

In another example, referring to the embodiment shown in FIGS. 10A and 10B, an elongate lead 130 has a central longitudinal axis 134, a marking 136 which is asymmetric with respect to central longitudinal axis 134, a directional electrode 122, and an electrical contact 128 to supply electrical connectivity to electrode 122. FIG. 10A shows a direct face-on view of marking 136, and FIG. 10B shows a see-through image 136' of marking 136 when elongate lead 130 is rotated 180°. In another example, referring to the embodiment shown in FIGS. 11A and 11B, an elongate lead 140 has a central longitudinal axis 144 and a marking 146 which is asymmetric with respect to central longitudinal axis 144. FIG. 11A shows a direct face-on view of marking 146, and FIG. 11B shows a see-through image 146' of marking 146 when elongate lead 140 is rotated 180°. Of course, the above described asymmetric features are only exemplary and other asymmetric features could also be used. For example a "C" shaped feature could also be used.

Figure 12A:
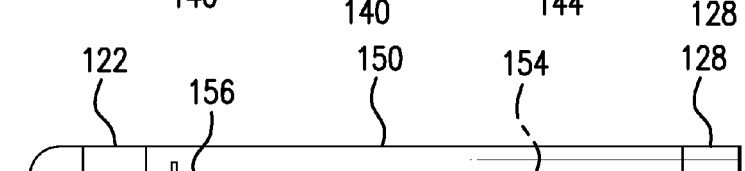
FIGS. 12A and 12B show side views of an elongate lead having a radiopaque feature that is symmetric with respect to the central longitudinal axis of the elongate lead.
Figure 12B:
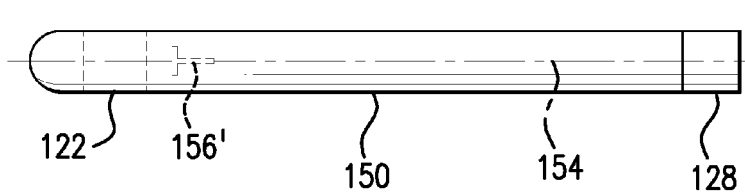

In a comparative example, referring to FIGS. 12A and 12B, a marking 156 is symmetric with respect to the central longitudinal axis 154 of elongate lead 150. The direct face-on view of marking 156 in FIG. 12A is identical to the see-through image 156' of marking 156 when elongate lead 150 is rotated 180°.

Figure 13A:
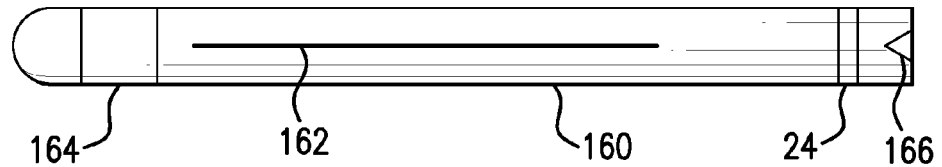
FIGS. 13A and 13B show side views of an elongate lead according to yet another embodiment.

In certain embodiments, the radiologically-visible feature(s) provides an image that becomes distorted when a proximal portion of the elongate lead is rotationally misaligned with a distal portion of the elongate lead (i.e., the elongate lead is twisted). By viewing the radiologic image of the radiologically-visible feature, the user can determine if there is any misalignment between proximal and distal portions of the elongate lead. For example, referring to the embodiment shown in FIGS. 13A and 13B, an elongate lead 160 has a directional stimulation electrode 164 at its distal portion and an electrical contact 24 to provide electrical connectivity to directional electrode 164. Elongate lead 160 also has an orientation indicator 166 which is aligned with the orientation of directional electrode 164. Elongate lead 160 also has a radiopaque feature in the form of a radiopaque stripe mark 162 on the surface of elongate lead 160.

Figure 13B:
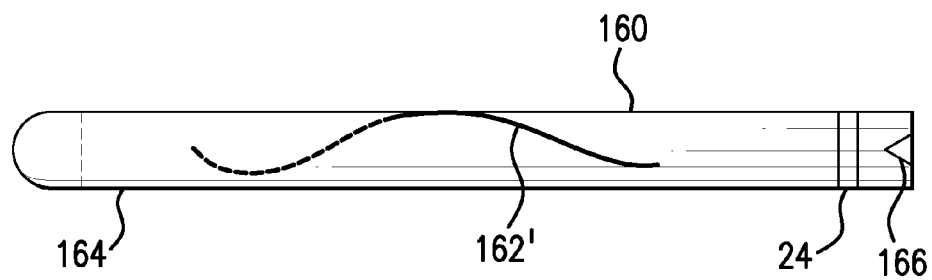

In operation, elongate lead 160 is inserted into the body and rotated at its proximal end to place electrode 164 in the desired orientation based on the alignment of orientation indicator 166. However, if rotational movement at the proximal end of elongate lead 160 is not fully translated to corresponding rotational movement at the distal end, the resulting twisting in elongate lead 160 will cause orientation indicator 166 to be misaligned with directional electrode 164. When viewed under x-ray fluoroscopy, as shown in FIG. 13B, it will be apparent that twisting in elongate lead 160 has caused stripe mark 162 to form a distorted image 162'. On this basis, the user will be aware of the twisting in elongate lead 160 and take appropriate action. Directional electrode 164 is then activated to provide electrical stimulation to the target site.

Figure 14A:
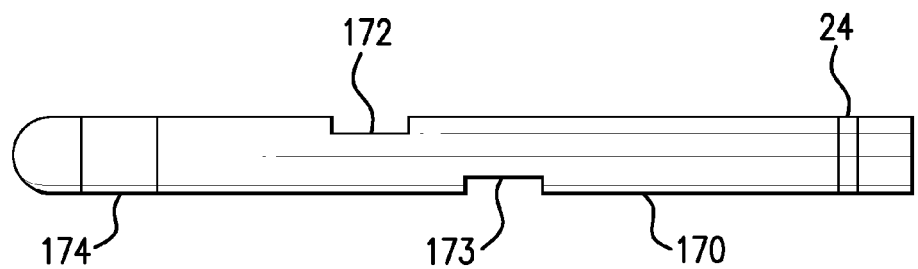
FIGS. 14A and 14B show side views of an elongate lead according to yet another embodiment.
Figure 14B:
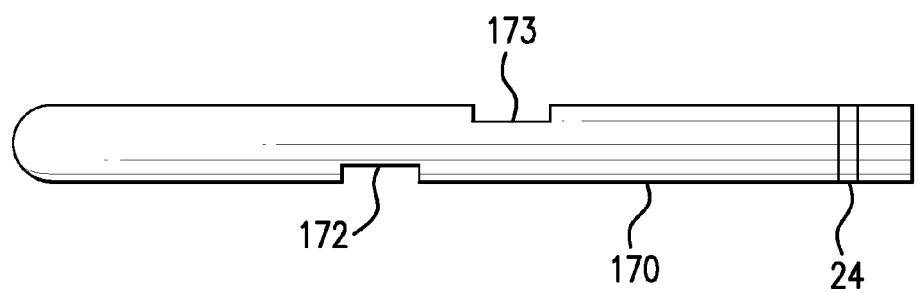

In some cases, the radiologically-visible feature is radiolucent. For example, referring to the embodiment shown in FIGS. 14A and 14B, an elongate lead 170 has a directional simulation electrode 174 at its distal portion and an electrical contact 24 to provide electrical connectivity to directional electrode 174. Elongate lead 170 also has two radiolucent cut-out windows, 172 and 173, that are adjacently positioned on opposite sides of elongate lead 170. FIG. 14A shows elongate lead 170 in one rotational orientation and FIG. 14B shows elongate lead 170 rotated 180° from the view shown in FIG. 14A. Based on the positions of radiolucent cut-out windows 172 and 173 under radiologic imaging, a user can determine the orientation of elongate lead 170 and/or directional electrode 174.

The radiologically-visible feature(s) may also be positioned anywhere along the length of the elongate lead, including proximal and distal portions. In some cases, the elongate lead may have two or more radiologically-visible features which are positioned in such a manner (e.g., alternating or staggered configurations) for more accurate determinations of orientation.

The material used to form the radiopaque feature(s) may be any of various radiopaque materials, such as metallic materials or semi-metallic materials. Non-limiting examples of materials include titanium dioxide, bismuth compounds, or barium sulfate. The radiopaque feature(s) can be affixed to the elongate lead in any of various ways, including applying as a surface marking, embedding within the wall of the elongate lead, or inserting within the elongate lead.

This second aspect of the present invention may be combined with any of the features in the first and/or third aspects of the present invention.

In any of the embodiments described above, the size, shape, configuration, and dimensions of the elongate lead will vary depending upon the particular application. For example, the shape of the elongate lead may be cylindrical, flat, conical, etc. Where the elongate lead is cylindrical, the diameter of the elongate lead may be in the range of about 0.5 to 1.50 mm, but other diameters are also possible, depending upon the particular application. The length of the elongate lead may be in the range of about 10 to 60 cm, but other lengths are also possible, depending upon the particular application. In some cases, the size, shape, configuration, and dimensions of the elongate lead are selected for use in electrical stimulation of brain structures. For example, co-pending application Ser. No. 10/602,319 (filed Jun. 24, 2003) describes various stimulation leads and electrodes which are suitable for use in the present invention. The material composition and mechanical properties (i.e. the flexibility) of the body of the elongate lead will vary depending upon the particular application. In some cases, the body of the elongate body is formed of a non-conductive material, such as a polymeric material, glass or quartz including silicone and/or polyurethane.

In any of the embodiments described above, the elongate lead has at least one stimulation electrode positioned at a distal portion of the elongate lead. The stimulation electrode is designed to provide electrical stimulation to a part of a patient's body (e.g., parts of the brain). As mentioned above, the stimulation electrodes are directional electrodes that extend less than 360° about the body of the elongate lead. This means that the stimulation electrode bands do not form a continuous electrode surface, but rather the electrode bands are segmented into a plurality of individual electrodes that are substantially isolated from each other. Individual electrodes can range in an angular distance around the exterior of the body of the elongate lead by as little as a few degrees to almost completely around the body of the lead. The radial span of the electrodes can be, for example, 120° about the body of the elongate lead. Of course, the elongate lead can also include, in addition to one or more directional electrodes, cylindrical electrodes that extend 360° about the body of the lead. Where the elongate lead has multiple electrodes, the electrodes may be electrically isolated from each other and selectively activated. This selective powerability of the electrodes provides a desired, focused (i.e. directed) electrical field around the body of the lead. The material composition, electrical properties (e.g., impedance), dimensions (e.g., height, width, axial spacing, and shape), and number (e.g., single or multiple) of the stimulation electrodes on the elongate lead will vary depending upon the particular application. For example, the electrodes may have a cylindrical shape, an oval shape, or a rectangular shape. In fact, the individual electrodes may take any variety of shapes to produce the desired focused and/or directional electric field.

In any of the embodiments described above, the lead guide and the delivery structure may have any of various shapes, sizes, dimensions, mechanical properties (e.g., stiffness), and material compositions, depending upon the particular application. For example, the lead guide and/or the delivery structure may be made of tungsten, stainless steel, MP35N, and may be coated with PTFEB, parylene, or ETFE. The lead guide should be rigid enough such that the distal end of the lead guide moves in unison with the proximal end when the lead guide is rotated. Similarly, the delivery structure should be rigid enough such that the distal end of the delivery structure moves in unison with the proximal end when the delivery structure is rotated.

In a third aspect, the present invention provides an electrode system for determining the position and/or rotational orientation of an electrode positioned within a body. The system comprises an elongate lead having at least one directional electrode positioned at a distal portion of the elongate lead and a position determining apparatus for determining the position and/or orientation of the electrode when the electrode is positioned in a body.

Any of various types of apparatuses for determining the position of a remote object can be used in the electrode system. The position and/or orientation may be determined within a one-dimensional, two-dimensional, or three-dimensional framework. In certain embodiments, the system uses remote signal detection for determining the position and/or orientation of an electrode. The remote signal may emitted from the electrode itself, or may be emitted from the body tissue being stimulated by the electrode (for example, brain waves that can be captured by EEG). As such, the position determining apparatus comprises a plurality of signal detection sensors, positioned externally (for example, on the scalp) or internally to the patient's body (for example, subcutaneously or on the cortex), for detecting the desired signal. The number and spatial positions of the signal detection probes will depend upon various conditions, such as the location of the target site, the strength of the signal, the desired resolution, and the desired number of positional axes (1-D, 2-D, or 3-D).

In some cases, the system comprises three or more signal detection probes to allow for triangulation of the electrode. For example, by triangulation based on the differential strengths of the detected signals from three signal detection probes (which will vary according to the distance of the signal detection probes from the signal), the x, y, z coordinates and the orientation of the electrode can be calculated. Any of various types of signal processing systems and computer systems can be used to process the signal and perform the mathematical calculations for determining the position and/or orientation of the electrode.

Figure 15:
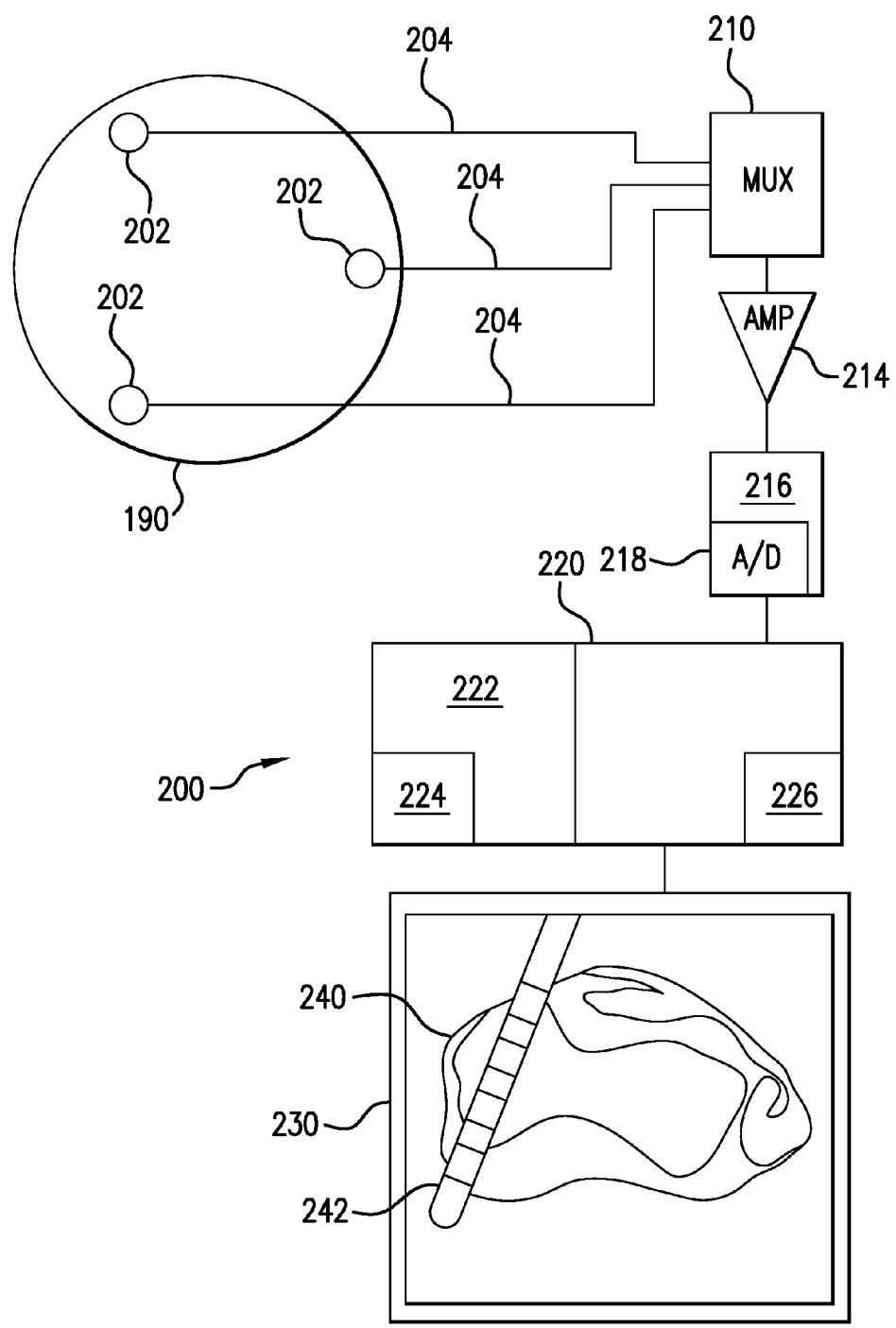
FIG. 15 shows an electrode system according to an embodiment of the present invention.

For example, referring to the embodiment shown in FIG. 15, an electrode system 200 comprises three EEG sensors 202 located on predetermined spatial positions on the top of a patient's head 190. Each of EEG sensors 202 are electrically coupled via wires 204 to separate input channels of a conventional multiplexer 210, which samples each sensor input channel in a time-multiplexed fashion. The selected EEG sensor signal is then input into an amplifier 214 and the amplified signal is sent to a signal processor 216 to process the signal. Signal processor 216 contains an analog-to-digital converter (A/D) 218 to convert the signals into digital form, which is then transmitted to a conventional computer 220 or clinician and/or patient programmer containing a microprocessor 226 and memory 222. Alternatively, a conventional EEG apparatus may be used in combination with the electrode system, with the EEG data being stored and then transferred to the electrode system.

Memory 222 is loaded with software 224 which is configured to establish an orthogonal three-dimensional coordinate system and receive spatial information about the relevant anatomic structures and/or other fiducial references, which is then stored in memory 222. Software 224 also receives and stores information about the spatial positioning of EEG sensors 202. Using any of various triangulation algorithms, software 224 then uses the signal data to calculate the position and/or orientation of the electrode inside the brain. A mapping function is then used to translate the calculated position and/or orientation into the reference frame of the stored coordinate system containing the fixed anatomic structures and/or other fiducial references (e.g., the AC-PC plane of the brain, or the neurosurgical stereotactic headframe). A three-dimensional composite image, showing a lead 240 and electrodes 242, is then displayed on a display screen 230. This three-dimensional image can be manipulated to provide various views, including coronal, sagittal, and axial views. In some cases, the volume of activation provided by electrodes 242 may also be displayed in conjunction with the relevant brain structures. This allows the user to adjust the orientation and/or position of lead 240, or adjust various stimulation parameters such as signal intensity or amplitude, to specifically target the relevant brain structures.

Figure 16:
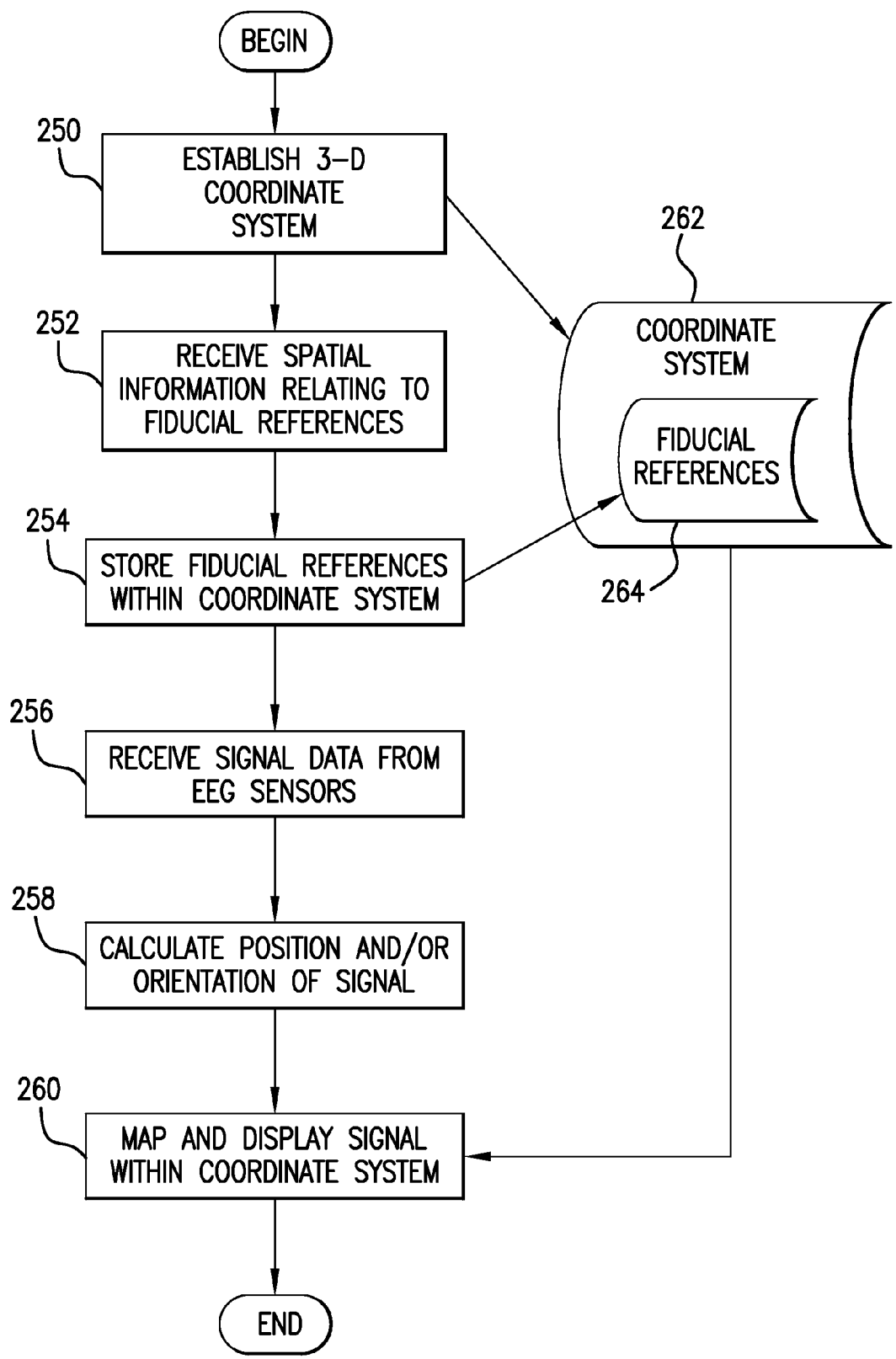
FIG. 16 shows a flowchart illustrating the processes performed by software within an electrode system according to yet another embodiment.

The flowchart in FIG. 16 illustrates the above-mentioned processes performed by software 224. Namely, software 224 establishes an orthogonal 3-D coordinate system (process blocks 250 and 262); receives spatial information about the fiducial references (process block 252); stores the fiducial references within the coordinate system (process blocks 254 and 264); receives signal data from the EEG sensors (process block 256); calculates the position and/or orientation of the signal (process block 258); and, maps and displays the signal within the stored coordinate system (process blocks 260 and 262).

In certain embodiments, the position determining apparatus uses any of various electromechanical position transducers for determining the position of the electrode based on the movement of the elongate lead and/or lead guide. For example, the linear motion actuation systems and/or navigation systems described in co-pending application Ser. No. 10/602,319 (filed Jun. 24, 2003) may be used in the position determining apparatus. Any of various types of signal processing systems and computer systems, including those mentioned above, can be used to process the signal and perform the mathematical calculations for determining the position and/or orientation of the electrode.

In certain embodiments, the position determining apparatus comprises a sensing electrode positioned on the elongate lead. The sensing electrode has an impedance suitable for detecting and/or recording an electrical signal from neural structures in the brain. Based on the characteristics of signals emitted by different neural structures, and by comparing with the electrical signals detected by the sensing electrodes, the position and/or orientation of the elongate lead may be determined. Any of various types of signal processing systems and computer systems, including those mentioned above, can be used to process the signal and perform the mathematical calculations for determining the position and/or orientation of the electrode.

In certain embodiments, the position determining apparatus comprises a computer system with a user interface for receiving manually inputted data which can be used to calculate the position and/or orientation of the electrode. For example, the position determining apparatus may receive manually inputted data for the location of the tip of the elongate lead (for example, as indicated by the stereotactic headframe), the rotational orientation of the elongate lead (for example, using the cannula holder shown in FIG. 5), and the angle of entry of the elongate lead (for example, as indicated by the stereotactic headframe via arc and ring coordinates). The system can then use this data to map the position and/or orientation into a coordinate system containing the fixed anatomic structures and/or other fiducial references (e.g., the AC-PC plane of the brain, or the neurosurgical stereotactic headframe).

This third aspect of the present invention may be combined with any of the features in the first and/or second aspects of the present invention.

The present invention may have any of various applications in electrical stimulation treatments. For example, in addition to brain stimulation, the present invention may be used for delivering electrical stimulation to the spinal cord, spinal nerve roots, ganglions, and other structures of the nervous system.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

We claim:

1. An elongate lead having a central longitudinal axis, a distal portion, and a proximal portion, the elongate lead comprising:
   at least one directional electrode positioned on the distal portion of the elongate lead; and
   at least one radiologically-visible feature positioned on the distal portion of the elongate lead for indicating an orientation of the at least one directional electrode when viewed in an image obtained under radiologic imaging, wherein the radiologically-visible feature comprises a first edge and a second edge and has an asymmetric shape such that:
      the first edge is parallel to the central longitudinal axis of the elongate lead;
      the second edge is opposite the first edge and parallel to the central longitudinal axis of the elongate lead; and
      in order to indicate the orientation of the at least one directional electrode, the asymmetric shape of the feature is configured and arranged, when viewed in a radiological image, to produce a first representation of the feature in the radiological image when the lead is in a first position and to produce a second representation of the feature in the radiological image when the lead is in a second position that is rotated 180 degrees about the central longitudinal axis from the first position, wherein the second representation of the feature is a mirror image of, and visually different from, the first representation of the feature.

2. The elongate lead of claim 1, wherein the radiologically-visible feature is radiopaque.

3. The elongate lead of claim 1, wherein the radiologically-visible feature is radiolucent.

4. The elongate lead of claim 1, wherein the elongate lead comprises two or more radiologically-visible features disposed on the elongate lead.

5. The elongate lead of claim 1, wherein the at least one directional electrode is aligned with the orientation of the radiologically-visible feature.

6. The elongate lead of claim 1, wherein the radiologically-visible feature is adapted to be viewed under CT imaging.

7. The elongate lead of claim 1, wherein the radiologically-visible feature is adapted to be viewed under MR imaging.

8. The elongate lead of claim 1, wherein the radiologically-visible feature is adapted to be viewed under x-ray imaging.

9. The elongate lead of claim 1, wherein the radiologically-visible feature is adapted to be viewed under x-ray fluoroscopy.

10. An elongate lead having a longitudinal axis, a proximal portion, and a distal portion, the elongate lead comprising:
    at least one directional electrode positioned on the distal portion of the elongate lead;
    an orientation indicator positioned on the proximal portion of the elongate lead, wherein the elongate lead is twistable between a non-twisted state and a twisted state by a rotational movement of the proximal portion of the lead that is not fully translated to the distal portion of the lead; and
    a radiologically-visible stripe mark positioned on the elongate lead and extending between the orientation indicator and the at least one electrode such that, in a radiological image, the stripe mark appears in the radiological image to be straight and parallel to the longitudinal axis of the elongate lead when the elongate lead is in the non-twisted state and appears in the radiological image to be helical when the elongate lead is in the twisted state.

11. The elongate lead of claim 10, wherein the radiologically-visible stripe mark is radiopaque.

12. The elongate lead of claim 10, wherein the radiologically-visible stripe mark is adapted to be viewed under x-ray imaging.

13. The elongate lead of claim 10, wherein the radiologically-visible stripe mark is adapted to be viewed under x-ray fluoroscopy.

* * * * *